(12) United States Patent
Bungay, III et al.

(10) Patent No.: US 8,535,936 B2
(45) Date of Patent: Sep. 17, 2013

(54) VESSELS FOR MIXING BIOPROCESSING MATERIALS

(75) Inventors: Henry R. Bungay, III, Troy, NY (US); James S. Bungay, Rexford, NY (US); John G. Sigsby, Glenmont, NY (US)

(73) Assignee: TwistaFerm, Troy, NY (US)

( * ) Notice: Subject to any disclaimer, the term of this patent is extended or adjusted under 35 U.S.C. 154(b) by 200 days.

(21) Appl. No.: 12/428,519

(22) Filed: Apr. 23, 2009

(65) Prior Publication Data

US 2009/0325282 A1 Dec. 31, 2009

Related U.S. Application Data

(60) Provisional application No. 61/133,505, filed on Jun. 30, 2008.

(51) Int. Cl.
*C12M 1/34* (2006.01)

(52) U.S. Cl.
USPC .................................. 435/288.7; 435/289.1

(58) Field of Classification Search
USPC ................... 383/3, 43, 44, 200, 906; 222/92; 366/225, 326.1
See application file for complete search history.

(56) References Cited

U.S. PATENT DOCUMENTS

| | | | |
|---|---|---|---|
| 737,768 A | 9/1903 | Preston | |
| 768,956 A | 8/1904 | Smithley | |
| 1,607,811 A | 11/1926 | Blum | |
| 2,511,291 A * | 6/1950 | Mueller | 366/181.5 |
| 2,553,071 A * | 5/1951 | Sant | 206/532 |
| 2,673,722 A | 3/1954 | Griffin et al. | |
| 3,207,420 A * | 9/1965 | Navarrete-Kindelan | 383/38 |
| 3,432,149 A | 3/1969 | Stalberg et al. | |
| 3,468,520 A | 9/1969 | Duryea et al. | |
| 3,518,393 A | 6/1970 | Besseling et al. | |
| 3,540,700 A | 11/1970 | Freedman et al. | |
| 3,819,158 A | 6/1974 | Sharpe et al. | |
| 3,833,203 A | 9/1974 | Garlinghouse | |
| 4,162,129 A | 7/1979 | Bartholemew, Jr. | |
| 4,373,029 A | 2/1983 | Nees | |
| 4,449,243 A * | 5/1984 | Platel | 383/103 |
| 4,548,606 A * | 10/1985 | Larkin | 604/414 |
| 4,608,043 A * | 8/1986 | Larkin | 604/87 |
| 4,762,794 A | 8/1988 | Nees | |
| 4,795,265 A | 1/1989 | Dahlberg et al. | |
| 4,852,641 A | 8/1989 | Noble | |
| 4,890,757 A | 1/1990 | Robbins, III | |
| 4,952,068 A * | 8/1990 | Flint | 366/337 |
| 5,008,197 A | 4/1991 | Wergeland et al. | |
| 5,225,346 A * | 7/1993 | Matsumiya et al. | 435/289.1 |
| 5,269,428 A | 12/1993 | Gilbert | |
| 5,335,591 A | 8/1994 | Pozar | |
| 5,482,854 A | 1/1996 | O'Leary et al. | |
| 5,669,520 A | 9/1997 | Simpson | |

(Continued)

OTHER PUBLICATIONS

Wave Bioreactor—FlexMixer—Part of GE Healthcare (2 pages) http://www.wavebiotech.com/wave_mixer/filesmixer.htm.

(Continued)

*Primary Examiner* — Michael Hobbs

(74) *Attorney, Agent, or Firm* — Stephen F. Swinton, Jr.; Hoffman Warnick LLC

(57) ABSTRACT

A flexible vessel for mixing a bioprocessing fluid has contact points or adhesions between its front and back walls to promote and guide flow patters for mixing the contents.

18 Claims, 2 Drawing Sheets

Examples of Locations of Contacts of Front Wall with Back

(56) References Cited

U.S. PATENT DOCUMENTS

| | | | |
|---|---|---|---|
| 5,697,701 A | 12/1997 | Forrest et al. | |
| 5,697,703 A | 12/1997 | Lucchetti | |
| 5,699,730 A | 12/1997 | Ogier et al. | |
| 5,779,974 A | 7/1998 | Kuzyk | |
| 6,142,661 A | 11/2000 | Lafond | |
| 6,165,778 A | 12/2000 | Kedar | |
| 6,190,913 B1 | 2/2001 | Singh | |
| 6,267,498 B1 | 7/2001 | Lafond et al. | |
| 6,273,600 B1 | 8/2001 | Sharpe | |
| 6,279,725 B1 | 8/2001 | McBrady et al. | |
| 6,312,151 B1 | 11/2001 | Pendleton | |
| 6,345,734 B2 | 2/2002 | Schalow et al. | |
| 6,391,638 B1* | 5/2002 | Shaaltiel | 435/383 |
| 6,416,212 B1 | 7/2002 | Rogers et al. | |
| 6,499,615 B1 | 12/2002 | Szieff et al. | |
| 6,503,455 B1* | 1/2003 | Kidd | 422/548 |
| 6,634,783 B2 | 10/2003 | Baron | |
| 6,637,929 B2 | 10/2003 | Baron | |
| 7,055,683 B2* | 6/2006 | Bourque et al. | 206/219 |
| 7,077,559 B2 | 7/2006 | Hlavinka et al. | |
| 7,348,175 B2 | 3/2008 | Vilendrer et al. | |
| 7,377,686 B2 | 5/2008 | Hubbard | |
| 7,658,542 B2* | 2/2010 | Risgalla | 383/44 |
| 7,799,521 B2 | 9/2010 | Chen | |
| 2003/0008389 A1 | 1/2003 | Carll | |
| 2004/0228208 A1 | 11/2004 | Papania et al. | |
| 2005/0263006 A1 | 12/2005 | Saha | |
| 2005/0277188 A1 | 12/2005 | Ellis et al. | |
| 2006/0019376 A1 | 1/2006 | Bungay et al. | |
| 2006/0182370 A1* | 8/2006 | Risgalla | 383/44 |
| 2008/0186802 A1 | 8/2008 | Bungay et al. | |

OTHER PUBLICATIONS

Bungay et al., "Disposable Bioreactors", 4 pages, http://www.tc-tech.com/.

Bowers, Applicant Bungay III, U.S. Appl. No. 12/026,054, Office Action Communication, dated Jul. 11, 2011, 21 pages.

Bowers, Applicant Bungay III, U.S. Appl. No. 11/186,610, Office Action Communication, RPI-0014, Dec. 31, 2009, 18 pages.

Bowers, Applicant Bungay III, U.S. Appl. No. 11/186,610, Office Action Communication, RPI-0014, Jun. 8, 2010, 18 pages.

Bowers, Applicant Bungay III, U.S. Appl. No. 11/186,610, Office Action Communication, RPI-0014, Mar. 4, 2009, 29 pages.

Bowers, Applicant Bungay III, U.S. Appl. No. 11/186,610, Office Action Communication, RPI-0014, Oct. 13, 2009, 15 pages.

* cited by examiner

VESSELS FOR MIXING BIOPROCESSING MATERIALS

CROSS-REFERENCE TO RELATED APPLICATIONS

This application claims the benefit of Provisional Application Ser. No. 61/133,505 filed Jun. 30, 2008 and is related to co-pending U.S. Applications 20060019376 A1 published Jan. 26, 2006 and U.S. No. 20080186802 A1, published Aug. 7, 2008 the entireties of which are incorporated by reference.

STATEMENT REGARDING FEDERALLY SPONSORED RESEARCH OR DEVELOPMENT

No aspect of this invention have received any support from a federal or state agency. All research and development were funded by Twistaferm.

TECHNICAL FIELD

The present invention relates generally to the field of fermentation devices and more specifically to a fermentation chamber for a mixing apparatus.

BACKGROUND OF THE INVENTION

The development and commercialization of many processes in the fields of medicine, chemistry, and agriculture require the use of fermentation devices or "bioreactors." As used herein, the term "fermentation" means a process for the production of a product by culturing cells or microorganisms, the process of culturing cells or microorganisms, or a process for the bioconversion of one material to another. In some bioprocesses, the organisms themselves are the desired product.

Cell culturing, for example, is often carried out in vessels that permit the contacting of cells with nutritive media and oxygen. In industrial applications, such processes are often carried out in very large vessels, often far greater than 1000 liters in capacity. During research and development, however, it is generally desirable to test such processes on a much smaller scale.

For many decades, bioprocessing research at a small scale had been conducted in Petri dishes, test tubes, flasks, and rigid bioreactors. Flasks have been agitated with rotary shakers, wrist-action shakers, or reciprocating shakers. Magnetic mixers are commonly used in various types of small bioreactors. It is now accepted that disposable, flexible plastic vessels have major advantages over the ancient technology. Several types of such disposable plastic bioreactors have been reported. One term for a disposable bioreactor is "biobag". To function well, a biobag must have effective means for agitation. Furthermore, many bioprocesses also require adequate concentrations of dissolved oxygen. Aeration and good mixing are factors in reaching an adequate concentration.

The biobag may be biocompatible and may be configured to hold bioprocessing fluid such as: culture medium for a fermentation as in the production of alcohol by yeast, culture medium inoculated with cells for tissue culture, biochemicals in solution to be transformed to other biochemicals by immobilized enzymes or immobilized cells also in the fluid, or growth medium for bacteria, yeast, molds, or other cells.

Hlavinka and Martinez recognized that mixing in a flexible bag can be promoted by uneven squeezing (U.S. Pat. No. 7,077,559). However, the uneven squeezing was achieved by having the external arms contact the bag at selected points or by having gaps in the arms to insure uneven contact. When a bag holds a different volume of liquid or when the bag does not hang exactly the same as another bag, the mixing patterns will not replicate well.

A need exists, therefore, for a device that avoids the above described limitations. Specifically, there is a need for a fermentation chamber and mixing apparatus that (1) will not damage delicate components of the liquid medium, such as living cells and microorganisms, (2) can provide sufficient agitation of the liquid medium to ensure proper mixing and/or aeration, (3) is inexpensive to produce and use.

SUMMARY OF THE INVENTION

The present invention provides a vessel (container) for mixing a bioprocessing fluid. This vessel can be associated with a mixing system described in our pending patent applications. The mixing device has arms that squeeze and release flexible portions of the vessel alternately. The novel feature of this improved vessel is the incorporation of contact points or guides that attach a small portion of the front wall of the flexible vessel to its back wall. These contacts serve two important functions. One is prevention of excess bulging that hinders close packing of the flexible containers. More important is the effect on mixing patterns. Squeezing action on a flexible bag without contacts creates mixing with little pattern or direction; the liquid level simply moves up and down as the biobag is squeezed and released, and there is little side-to-side motion. The contact points or guides direct the flow for a better defined and more efficient mixing with circulation up, down, and sideways. Our invention creates the desired mixing patterns by altering the flexible bag itself. Our tests have shown that external devices such as described by Hlavinka and Martinez can indeed create favorable mixing patterns but not to the extent observed with the bag that has points or guides of contact between the front and back walls of the bag itself.

BRIEF DESCRIPTION OF THE DRAWINGS

The subject matter which is regarded as the invention is particularly pointed out and distinctly claimed in the claims at the conclusion of the specification. The foregoing and other features, and advantages of the invention will be readily understood from the following detailed description of preferred embodiments taken in conjunction with the accompanying drawings in which:

DETAILED DESCRIPTION OF THE INVENTION

In accordance with the principles of the present invention, systems and methods for mixing bioprocessing materials are provided.

This flexible bioreaction chamber can be agitated by alternately squeezing and releasing it. Our pending patent application discloses a device that does so for a multiplicity of biobags, but this new invention also works well with a squeezing mechanism for a single biobag. We have disclosed squeezing and releasing with a bar or bars that touch the bag in its lower portion. The precise location of these bars greatly affects the mixing action. Although optimized for our previous invention of a squeezing machine, this new invention is applicable to other methods for agitation of a biobag. Nees also mixes bags by distorting them (U.S. Pat. No. 4,762,794) but with two chambers so that the liquid moves from one to another.

U.S. Patent Application Publication No. 2003/0008389 to Carll describes a disposable cell culture vessel with a hollow sleeve in its interior, into which is placed a magnetic stirrer. In some embodiments, the sleeve is fitted with a flexible blade. This creates a gentle stirring of the cells, which keeps the cells in suspension and prevents the cells from shearing. Where more vigorous agitation or greater aeration of the liquid medium is needed, such a device is inadequate.

Attempts have been made to eliminate the need for internal mixing mechanisms altogether. U.S. Pat. No. 4,373,029 to Nees, and U.S. Pat. No. 3,540,700 to Freedman et al., for example, describe devices for pivotally rotating vessels containing cells and a nutrient medium. There is a limit, however, to the degree of mixing attainable with such devices. For example, Nees notes that "acceleration magnitudes are essentially determined only by the gravity of the micro carrier in the earth's gravitational field, reduced by the viscosity of the nutrient solution." Col. 2, lines 11-14. Thus, for processes requiring a greater degree of mixing or agitation, including, for example, processes requiring greater aeration of the liquid medium, such devices are not useful.

Fluids in bags can be mixed with application of peristaltic forces as described by Hubbard, U.S. Pat. No. 7,377,686 This type of disposable bag incorporates a semi-permeable membrane through which gases can diffuse.

Singh, U.S. Pat. No. 6,190,913 describes a method with no internal mixers that places a bag on a rocker. The rocker tilts the bag first one way and then the other to induce mixing.

Figure 1:
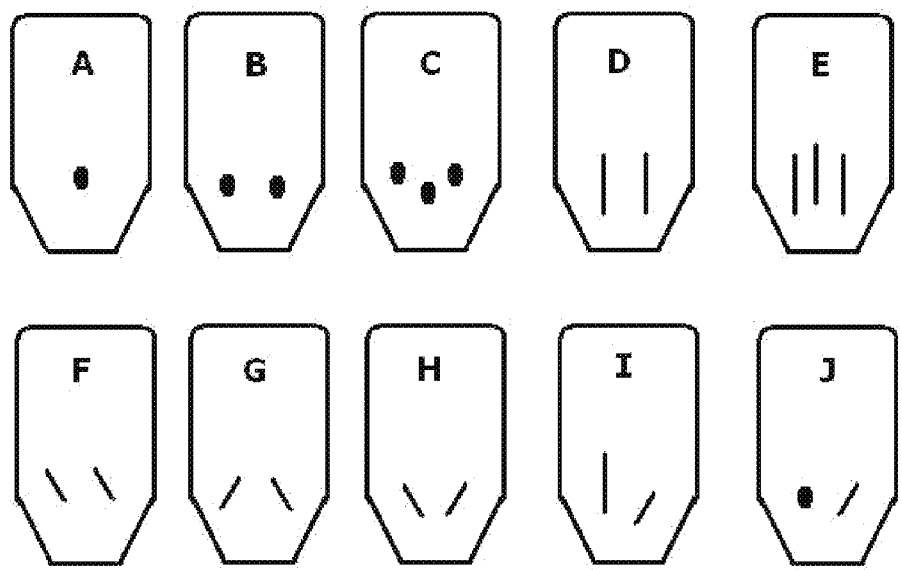
FIG. 1 shows a variety of places where the front and back walls of a flexible bag can be connected. These designs are by no means limiting because an infinite number of variations is possible. Arrangements such as FIG. 1-H are among the best for developing excellent flow patterns.

In an exemplary embodiment depicted in FIG. 1, designs of a flexible vessel for bioprocessing are shown. Any of the designs that attach a portion of the front wall of the vessel to the back wall prevent excess bulging of the vessels when filled with fluid, but some arrangements also promote superb mixing. The designs with slanted lines of contact allow fluid to rise in the central portion of the vessel when it is squeezed, and the fluid tends to fall back in the outer regions of the vessel when squeezing is released. These flow patterns insure adequate mixing that is superior to the mixing in bags with no added contact points or lines.

A biobag with only one contact or guide should be squeezed on only one side or squeezed unevenly to induce a circulation pattern. These circulation patterns are inferior to those with two or more contacts in our experiments but can be better than with no contact points. Bags with multiple contacts can also be squeezed unevenly at a location below these contacts because the contacts are obstructions that tend to create defined mixing patterns. However, uneven squeezing is unnecessary when the contact points are located optimally.

The design of FIG. 1-G is highly effective for mixing. The location of the squeezing action is important; good squeezing requires having the arms touch below the contact lines or points. For those bioprocesses that require a high concentration of dissolved oxygen, the vessel can have an aeration tube. When this tube extends below the surface of the fluid in the vessel, bubbling contributes to the mixing.

Figure 2:
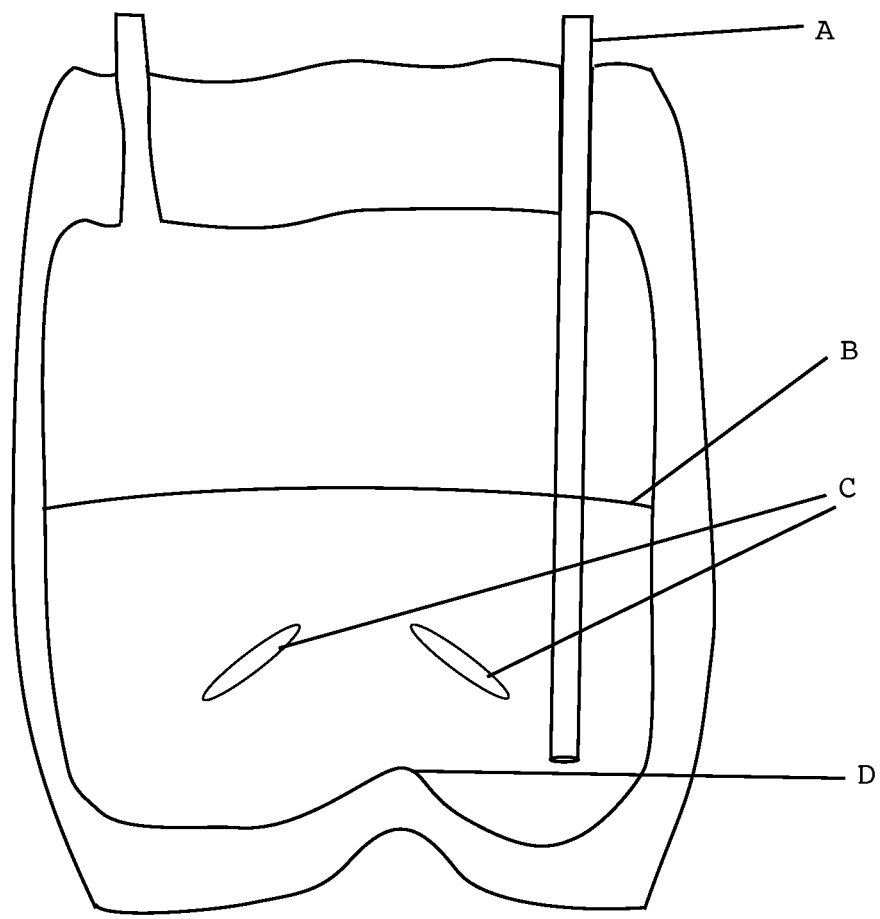
FIG. 2 shows a flexible bag with contacts between its front and back walls. This bag is designed to be squeezed about half way between its bottom and the contacts.

FIG. 2 shows a flexible bag with contacts between its front and back walls. A bag without these contacts is extended and distorted when filled with liquid and sags noticeably at its bottom. The bottom bulge is the limiting factor in determining how closely bags can be packed without touching each other. Incorporating these contacts greatly restricts the amount of bulging and permits closer packing. More importantly, the effect on mixing is highly advantageous. The labels are as follows: A. Typical port, but caps, sleeves, and other kinds of entry ports do not change the beneficial mixing in a bag with contact points. B. Indicates the surface of the liquid in the bag. This bag functions well with volumes that fill the bag to different levels. C. This shows two tilted lines of contact. The apparent line between them is a fold of the bag; there is no contact between the front and back walls along this line when the bag contains fluid. D. This is a pucker or dimple that forms when a bag contains fluid. Attempts to minimize this pucker were counterproductive because the pucker changes as the arms squeeze the bag. In other words, the pucker contributes to the better mixing observed in a bag with contacts between the front and back walls.

Many of the other means of mixing fluids in a bag can benefit from contact points or guides that help to define flow patterns. Bars that squeeze and release a bag are suited to bags that hang. Our pending patent is for a machine that handles multiple bags. However, any method for inducing flow in a bag can benefit from contact points or guides. The bag can be distorted by an outer bag that gets compressed gas to inflate and to deflate when gas pressure is reduced. Guiding the flow with the contact points or guides will improve mixing. This is true also for bag placed on a rocking platform. Another way to move the liquid in a bag is to lift or fold a portion of the bag below the liquid surface. This or any method of moving liquid in a bag will have better mixing when contact points or guides are employed.

While this invention has been described in conjunction with the specific embodiments outlined above, it is evident that many alternatives, modifications, and variations will be apparent to those skilled in the art. Accordingly, the embodiments of the invention as set forth above are intended to be illustrative, not limiting. Various changes may be made without departing from the spirit and scope of the invention as defined in the following claims:

| REFERENCES | | | |
| --- | --- | --- | --- |
| U.S. Pat. No. | Issue Date | Inventor(s) | Title |
| 7,077,559 | Jul. 18, 2006 | Hlavinka, D. J. and Martinez M. A. | Container or bag mixing apparatuses and/or methods |
| 6,190,913 | Feb. 20, 2001 | Singh, V. | Method for culturing cells using wave-induced agitation |
| 7,377,686 | Apr. 7, 2004 | Hubbard; J. D. | Peristalic mixing and oxygenation system |

-continued

REFERENCES

| 4,373,029 | Feb. 8, 1983 | Nees, S | Device for cultivation of matrix-bound biologic cell systems |
| 3,540,700 | Nov. 17, 1970 | Freedman | |
| 4,762,794 | Aug. 9, 1988 | Nees, S | Apparatus for contacting biological cell systems with a perfusion fluid |

| Publication No. | Publication Date | Inventors | Title |
| --- | --- | --- | --- |
| 20060019376 A1 | Jan. 26, 2006 | Bungay, H.R., Bungay, J.S, and Sigsby, J.G | Fermentation chamber and mixing apparatus |
| 20080186802 A1 | Aug. 7, 2008 | Bungay, H.R., Bungay, J.S, and Sigsby, J.G | Systems and methods for mixing bioprocessing materials |
| 20040142462 A2 | Jul. 22, 2004 | Carll, K. | Disposable Vessel |

What is claimed is:

1. A vessel comprising:
a flexible first surface having at least one edge;
a flexible second surface adjacent the first surface having at least one edge fixedly joined to the at least one edge of the flexible first surface, thereby forming a space between the flexible first surface and the flexible second surface, the space including:
a fluid containment portion extending from a bottom of the vessel upward to about half an overall height of the vessel, the fluid containment portion including at least two contact points between the flexible first surface and the flexible second surface at which a portion of the flexible first surface is in contact with a portion of the flexible second surface, forming a continuous void around and between each of the at least two contact points and between the flexible first surface and the flexible second surface; and
a headspace portion extending from a top of the vessel downward to the fluid containment portion between the flexible first surface and the flexible second surface, the headspace portion being free of contact points between the flexible first surface and the flexible second surface; and
at least one aeration tube extending from a top of the vessel between the flexible first surface and the flexible second surface and into the fluid containment portion.

2. The vessel of claim 1, wherein the at least two contact points substantially prevent bulging adjacent the continuous voids in response to the pressure within the fluid containment portion.

3. The vessel of claim 1, wherein the at least two contact points are capable of impeding movement of a liquid between the fluid containment portion and the headspace portion.

4. The vessel of claim 1, wherein the at least two contact points are positioned between the bottom of the vessel and a point above the bottom of the vessel between about one quarter and about one half the overall height of the vessel.

5. The vessel of claim 4, wherein the at least two contact points include a pair of ovoid contact points.

6. The vessel of claim 4, wherein the at least two one contact points include at least three ovoid contact points.

7. The vessel of claim 4, wherein the at least two one contact points include a pair of elongate contact points, each of which is oriented substantially vertically, with a first end nearer the bottom of the vessel and a second end nearer the top of the vessel.

8. The vessel of claim 4, wherein the at least two contact points include at least three elongate contact points, each of which is oriented substantially vertically, with a first end nearer the bottom of the vessel and a second end nearer the top of the vessel.

9. The vessel of claim 4, wherein the at least two contact points include a pair of elongate contact points, each of which is oriented at an angle, with a first end nearer the bottom of the vessel and a second end nearer the top of the vessel, the second end being angled from a substantially vertical orientation.

10. The vessel of claim 9, wherein each of the pair of elongate contact points has substantially the same angle.

11. The vessel of claim 9, wherein the second end of each of the pair of elongate contact points is angled inward toward a center of the vessel.

12. The vessel of claim 11, wherein the vessel contains a pucker along a bottom of the vessel when the fluid containment portion contains a fluid.

13. A vessel comprising:
a flexible first surface having at least one edge; and
a flexible second surface adjacent the first surface having at least one edge fixedly joined to the at least one edge of the flexible first surface, thereby forming a space between the flexible first surface and the flexible second surface, the space including:
a fluid containment portion extending from a bottom of the vessel upward to about half an overall height of the vessel, the fluid containment portion including at least two contact points between the flexible first surface and the flexible second surface at which a portion of the flexible first surface is in contact with a portion of the flexible second surface, forming a continuous void around and between the at least two contact points and between the flexible first surface and the flexible second surface; and
a headspace portion extending from a top of the vessel downward to the fluid containment portion between the flexible first surface and the flexible second surface, the headspace portion being free of contact points between the flexible first surface and the flexible second surface.

14. The vessel of claim 13, wherein the at least two one contact points are positioned between the bottom of the vessel and a point above the bottom of the vessel between about one quarter and about one half the overall height of the vessel.

15. The vessel of claim 14, wherein the at least two contact points include at least two elongate contact points, each of which is oriented at an angle, with a first end nearer the bottom of the vessel and a second end nearer the top of the vessel, the second end being angled from a substantially vertical orientation.

16. The vessel of claim 15, wherein the second end of each of the at least two elongate contact points is angled inward toward a center of the vessel.

17. The vessel of claim 16, wherein the vessel contains a pucker along a bottom of the vessel when the fluid containment portion contains a fluid.

18. The vessel of claim 15, wherein the second end of each of the at least two elongate contact points in angled outward toward a side of the vessel.

* * * * *